United States Patent [19]

Saito

[11] 4,345,342

[45] Aug. 24, 1982

[54] VACUUM SUCTION TYPE URINATING AID

[75] Inventor: Shuiichi Saito, Funabashi, Japan

[73] Assignee: Kimura Bed Mfg. Company Limited, Tokyo, Japan

[21] Appl. No.: 179,884

[22] Filed: Aug. 20, 1980

[30] Foreign Application Priority Data

Mar. 14, 1980 [JP] Japan ............................ 55-33372[U]
Mar. 14, 1980 [JP] Japan ............................ 55-33373[U]

[51] Int. Cl.[3] .......................... A61F 5/44; A61M 1/00

[52] U.S. Cl. ......................................... 4/301; 4/144.3; 4/305; 128/278; 128/295; 128/762

[58] Field of Search .................. 4/301, 302, 305, 431, 4/434, 435, 437, 144.1-144.4, 316, 450, 454, 457, 462, 463; 128/276, 278, 295, 760, 762, 765, 766, 763

[56] References Cited

U.S. PATENT DOCUMENTS

| | | | |
|---|---|---|---|
| 2,749,558 | 6/1956 | Lent et al. | 4/316 X |
| 3,811,135 | 5/1974 | Drochard, Jr. et al. | 4/435 |
| 4,084,589 | 4/1978 | Kulvi | 128/295 X |
| 4,168,548 | 9/1979 | Cantrell | 4/431 X |
| 4,281,655 | 8/1981 | Terauchi | 4/305 X |

*Primary Examiner*—Stuart S. Levy
*Attorney, Agent, or Firm*—Wenderoth, Lind & Ponack

[57] ABSTRACT

A vacuum suction type urinating aid, includes the urine transport tubes of plural urine suction units connected to a common urine tank through corresponding solenoid valves. The urine tank is connected at its upper part, to a vacuum suction device. Each of the plural urine suction units is composed of a urine receiver provided with a urine suction opening to be applied to a urinating region, an air suction hole separate from the urine suction opening, and a urine outlet, with one of the urine transport tubes being connected to the urine outlet of a respective urine receiver.

2 Claims, 5 Drawing Figures

VACUUM SUCTION TYPE URINATING AID

BACKGROUND OF THE INVENTION

The present invention relates to a vacuum suction type urinating aid.

There are people who must be assisted in urinating in bed. These people include the old lying in bed, serious patients, patients suffering from the incontinence of urine, etc. who cannot control their urination as soon as they feel a desire to urinate, and patients who cannot go to the toilet alone.

To attain the objective of assistance, an apparatus in which a receiver applied to the urinating region of the patient to receive his urine is connected with a tank to collect the urine through a tube has been used hitherto. However, with the conventional apparatus, the urine received by the receiver is dropped into the tank through the tube simply by gravity, and therefore the tube and the tank must be placed below the receiver, to enable the urine to by gravity. For example, if the patient changes his position, causing the tube to be placed even partially above the receiver, the urine in the tube flows back into the receiver, to soak the patient and bedclothes inconveniently. Such a conventional apparatus is disadvantagely restricted in the place of use and urinating pose.

SUMMARY OF THE INVENTION

The urinating aid of the present invention receives the urine of the patient in a urine receiver applied to his urinating region, and transports it to a urine tank through a urine transport tube forcedly together with air by vacuum suction, thereby overcoming the disadvantage of the conventional apparatus perfectly. In other words, even when the urine transport tube and the urine tank cannot be placed below the urine receiver, the present invention allows urine to be transported into the urine tank, without allowing any urine to flow back.

Particularly, the vacuum suction type urinating aid of the present invention has its components made common as far as possible, to enable plural patients to use the aid by sharing, to reduce the space of installation, for effective utilization of the space in a hospital and for reduction of equipment cost.

BRIEF DESCRIPTION OF THE DRAWINGS

The present invention is described below in detail with reference to the accompanying drawings which show embodiments of the invention.

DETAILED DESCRIPTION OF THE INVENTION

Figure 1:
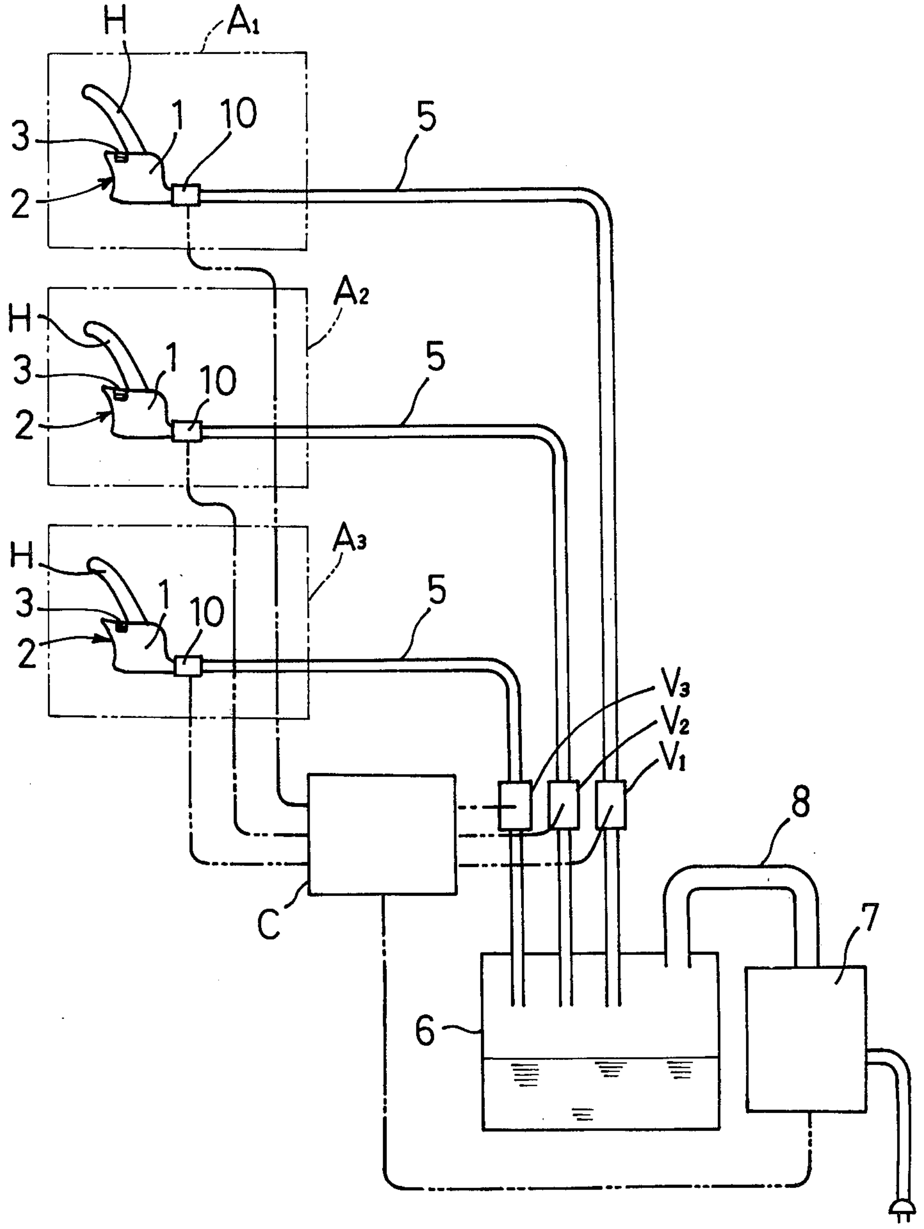
FIG. 1 is a systematic illustration showing the general composition of a first embodiment of the vacuum suction type urinating aid of the present invention.
Figure 4:
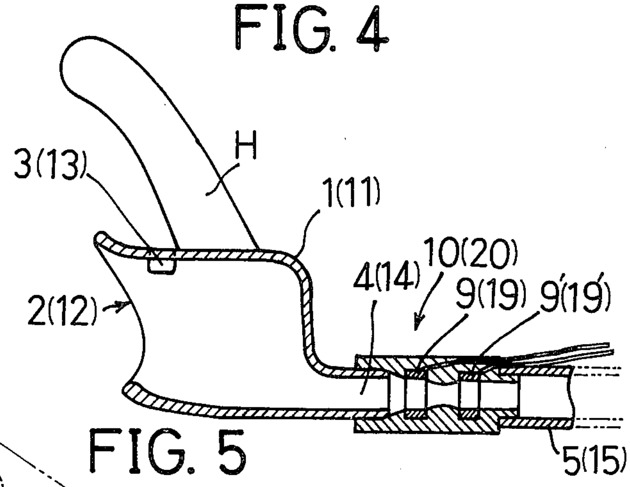
FIG. 4 is an enlarged illustrative sectional view of a main portion showing an embodiment of the urine receiver.
Figure 5:
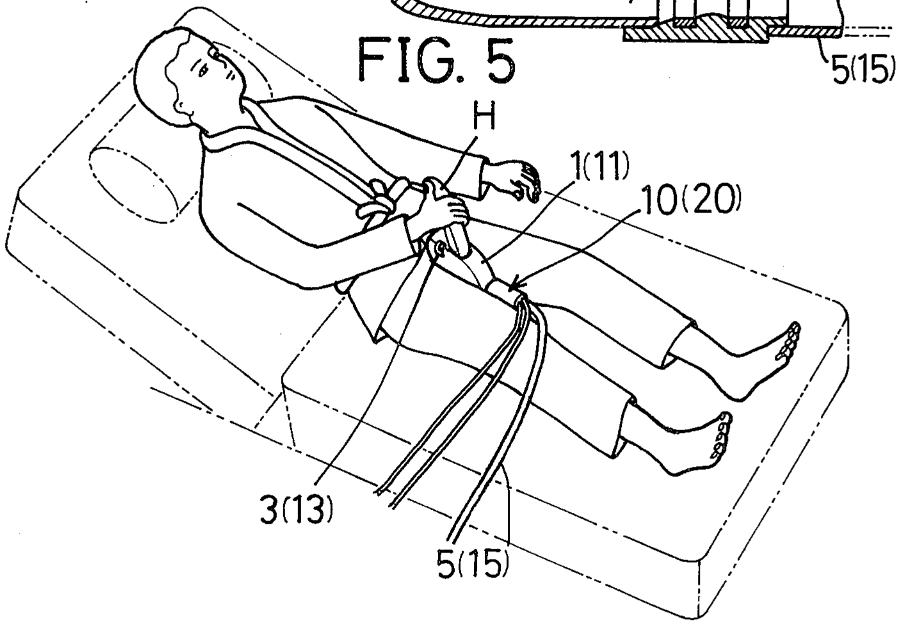
FIG. 5 is an illustrative perspective view showing the manner of use of the present invention.

The composition and operation of a first embodiment of the present invention are described below. In FIG. 1 there are shown plural urine suction units symbol and in each 1 is a urine receiver provided with a urine suction opening 2 to be applied to a urinating region and with an air suction hole 3 separate from urine suction opening 2. Urine reciever 1 is connected, at a urine outlet 4 (FIG. 4), to one end of a urine transport tube 5, to form a urine suction unit A. The other ends of the respective urine transport tubes 5 of urine suction units A ($A_1$, $A_2$, $A_3$, . . . ) are connected through respective solenoid valves V ($V_1$, $V_2$, $V_3$, . . . ) to a common urine tank 6, and urine tank 6 is connected, at is upper part, to a vacuum suction device 7. In FIG. 1 vacuum suction device 7 is connected with the top of the urine tank 6 by a vacuum suction tube 8, but urine tank 6 and vacuum suction device 7 can be combined solidly, or they may be adjoin each other by connection with a proper air duct, etc.

In this composition of the first embodiment of the present invention, for example, the urine suction units A ($A_1$, $A_2$, $A_3$, . . . ) are provided in correspondence with the number of patients in the same room in a hospital, etc., with the common urine tank 6 installed in a proper place in the room, and the urine transport tubes 5 of the respective urine suction units A ($A_1$, $A_2$, $A_3$, . . . ) are connected with the urine tank 6 through the respective solenoid valves V ($V_1$, $V_2$, $V_3$, . . . ), and urine tank 6 is connected, at its upper part, with the vacuum suction tube 8 communicating to vacuum suction device 7, so that each of the urine suction units A ($A_1$, $A_2$, $A_3$, . . . ) may control vacuum suction device 7 and the corresponding solenoid valve V ($V_1$, $V_2$, $V_3$, . . . ).

When a patient feels a desire to urinate, he applies the urine suction opening 2 of the urine receiver 1 of his urine suction unit A ($A_1$, $A_2$, $A_3$, . . . ) to his urinating region by holding the handle H, to urinate into urine receiver 1. Immediately before or after this action, a respective manual start switch is turned on, or for example, a pair of ring-shaped electrodes 9 (FIG. 4) and 9' provided at the urine outlet 4 detects a drop of resistance by the urine wetting the area between electrodes 9 and 9', to automatically turn on a respective start switch 10, thereby starting vacuum suction device 7 and simultaneously operating the respective solenoid valve V ($V_1$, $V_2$, $V_3$, . . . ) to be open. Thus, since vacuum pressure is applied to respective urine transport tube 5 of the urine suction unit A ($A_1$, $A_2$, $A_3$, . . . ) corresponding to the open solenoid valve V ($V_1$, $V_2$, $V_3$, . . . ), the urine received by respective urine receiver 1 is sucked and transported forcedly from the urine outlet 4 into the urine transport tube 5 together with the air sucked into the urine receiver 1 from air suction hole 3 and the clearance between the urine suction opening 2 and the urinating region, and is discharged through the corresponding solenoid valve V ($V_1$, $V_2$, $V_3$, . . . ) into the common urine tank 6, as mentioned before. In this case, since the vacuum suction tube 8 communicating to the vacuum suction device 7 is connected to the upper part of the urine tank 6, urine is collected in the urine tank 6, not being sucked into vacuum suction tube 8, to be separated from the air. Furthermore, since the air suction hole 3 is formed separately from the urine suction opening 2 in the urine receiver 1 of each urine suction unit A ($A_1$, $A_2$, $A_3$, . . . ), it prevents the urine suction opening 2 from adhering to the urinating region of the patient which otherwise would be caused by the vacuum pressure, to improve the feeling of using the aid, and even if the urine suction opening 2 is in close contact with the urinating region without any clearance, the volume of air required to carry the urine can be secured by the air sucked from air suction hole 3, 3. The opening of the air suction hole 3 can be made freely adjustable. Thus, in the present invention, since the urine received by the urine receiver 1 is forcedly sucked together with the sucked air from the urine outlet 4 into the urine transport tube 5, being discharged into the common urine tank 6 through the corresponding solenoid valve V ($V_1$, $V_2$, $V_3$, . . . ), urine does not flow back even when urine transport tube 5 is not placed below the urine receiver 1, and urine does not become spilled even if the patient moves his body during the use of the aid to position the urine transport tube 5 partially above the urine receiver 1.

Figure 3:
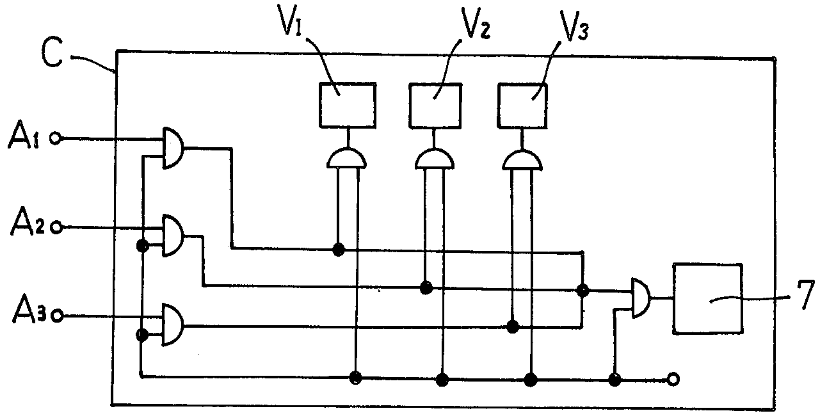
FIG. 3 is a circuit diagram showing an example of a control circuit.

In the first embodiment of the present invention, as mentioned above, since vacuum suction device 7 and the respective solenoid valves V ($V_1$, $V_2$, $V_3$, . . . ) can be controlled by start switches 10 individually in urine suction units A ($A_1$, $A_2$, $A_3$, . . . ), plural patients can urinate as they like, even simultaneously. Thus, the present invention has a feature that the urine tank 6, the vacuum suction tube 8 and the vacuum suction device 7 can be shared by plural patients, to reduce the space of installation and to lower costs. The control circuit C which enables the vacuum suction device 7 and the respective solenoid valves V ($V_1$, $V_2$, $V_3$, . . . ) to be controlled by urine suction units A ($A_1$, $A_2$, $A_3$, . . . ) individually can be composed as required, e.g. as shown in FIG. 3.

Figure 2:
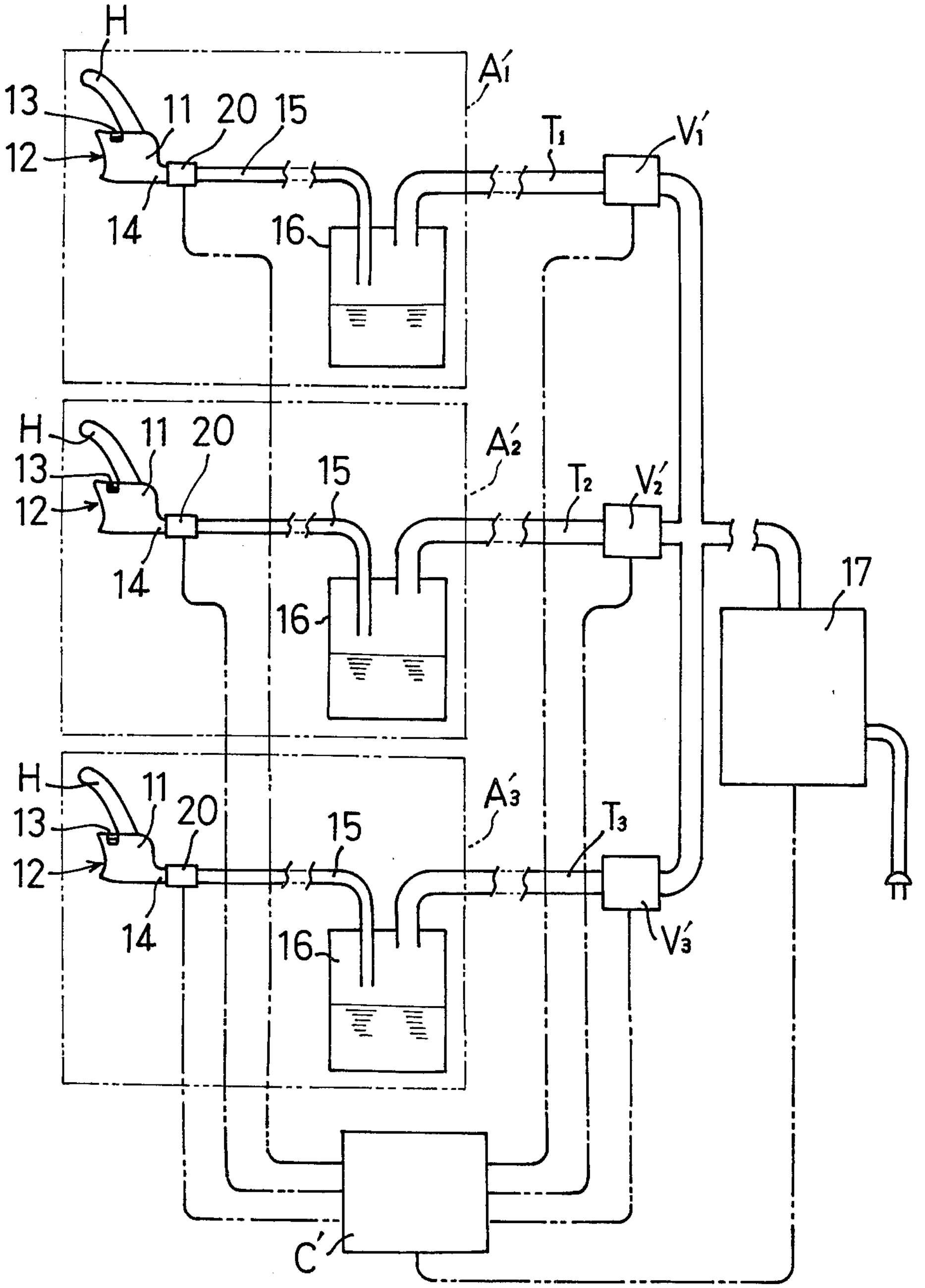
FIG. 2 is a systematic illustration showing the general composition of a second embodiment of the present invention.

The composition and operation of a second embodiment of the present invention are described below. In FIG. 2 there are shown plural urine suction units symbol and in each 11 is a urine receiver provided with a urine suction opening 2 to be applied to a urinating region and with an air suction hole 13 separately from urine suction opening 2. and Urine receiver 11 is connected, at its urine outlet 14, to one end of a urine transport tube 15, while the other end of urine transport tube 15 is connected to a urine tank 16, to form a urine suction unit A'. The urine tanks 16 of the respective urine suction units A' ($A'_1$, $A'_2$, $A'_3$, . . . ) are connected, at their upper parts, to respective vacuum suction tubes T ($T_1$, $T_2$, $T_3$, . . . ) branching from a common vacuum suction device 17, and solenoid valves V' ($V'_1$, $V'_2$, $V'_3$, . . . ) corresponding to the respective urine suction units A' ($A'_1$, $A'_2$, $A'_3$, . . . ) are provided in the passages of air current before the branching position.

In this composition, the urine suction units A' ($A'_1$, $A'_2$, $A'_3$, . . . ) are provided for the respective patients in the same room, for example, in a hospital, and the respective urine tanks 16 are connected, at their upper parts, to the vacuum suction tubes T' ($T'_1$, $T'_2$, $T'_3$, . . . ) branching from the common vacuum device 17. Urine suction units A' ($A'_1$, $A'_2$, $A'_3$, . . . ) are arranged to be able to individually control vacuum suction device 17 and the corresponding solenoid valves V' ($V'_1$, $V'_2$, $V'_3$, . . . ). The control circuit C' can be composed as required, e.g. in a manner similar to FIG. 3.

When a patient feels a desire to urinate, he applies the urine suction opening 12 of the urine receiver 11 of his urine suction unit A' ($A'_1$, $A'_2$, $A'_3$, . . . ) to his urinating region, to urinate into his urine receiver 11. Immediately before or after this action, a manual start switch is turned on, or for example, a pair of ring-shaped electrodes 19 and 19' provided at the urine outlet 14 detects a drop of resistance by the urine wetting the area between electrodes 19 and 19', to automatically turn on a respective start switch 20, thereby starting vacuum suction device 17 and simultaneously operating the corresponding solenoid valve V' ($V'_1$, $V'_2$, $V'_3$, . . . ) to be open. Thus, since vacuum pressure is applied to the urine tank 16 of the urine suction unit A' ($A'_1$, $A'_2$, $A'_3$, . . . ) corresponding to the open solenoid valve V' ($V'_1$, $V'_2$, $V'_3$, . . . ), the urine received by the urine receiver 11 is sucked forcedly from the urine outlet 14 into the urine transport tube 15 and transported together with the air sucked into the urine receiver 11 from air suction hole 13 and the clearance between the urine suction opening 12 and the urinating region, and is discharged into the urine tank 16. In this case, since the respective vacuum suction tube T ($T_1$, $T_2$, $T_3$, . . . ) communicating to the vacuum suction device 17 is connected to the upper part of the respective urine tank 16, urine is collected in the urine tank 16, is not being sucked by the respective vacuum suction tube T ($T_1$, $T_2$, $T_3$, . . . ), and is separated from the air. Also in the second embodiment of the present invention, since common vacuum suction device 17 and the respective solenoid valves V' ($V'_1$, $V'_2$, $V'_3$, . . . ) can be controlled by start switches 20, etc. individually by the respective urine suction devices A' ($A'_1$, $A'_2$, $A'_3$, . . . ), plural patients can urinate as they like even simultaneously. Thus, the present invention has a feature that the common vacuum suction device 17 can be shared by plural patients, to reduce the space of installation and to lower costs. In the meantime, if vacuum suction device 17 is installed outside the sickroom, or is housed in a sound-proof box, to be placed in a corner of a room, the generation of noise by the operating sound of vacuum suction device 17 can be prevented, as an effect of not disturbing other patients in the same room during use at night, etc.

As described above in detail, the present invention is not restricted in the place of use or urinating pose and is very effective as a urinating aid for serious patients, the old lying in bed, patients suffering from the incontinence of urine, etc., since urine received by the urine receivers is forcedly sucked together with air into urine transport tubes by a vacuum suction device, and is fed to urine tanks, to be collected in the urine tanks, and separated from air. Particularly, the present invention has an important feature that a vacuum suction device or a vacuum suction device, a urine tank and a vacuum suction tube can be shared by plural patients, to reduce the space of installation, for effective use of the space of a common sickroom, etc. and to lower the cost of installation.

What is claimed is:

1. A vacuum suction type urinating aid capable of simultaneous use by plural subjects, said aid comprising:
   - a plurality of urine suction units capable of simultaneous use by different subjects, each said unit including a urine receiver having a urine suction opening adapted to be applied to the urinating region of a particular subject to receive therefrom urine, an air suction opening separate from said urine suction opening, and a urine outlet, a urine tank, and a urine transport tube connected between said urine outlet and said urine tank;
   - a plurality of vacuum suction tubes, each said vacuum suction tube having a first end connected to an upper portion of a respective said urine tank and a second end;

each said vacuum suction tube having therein a respective valve movable between a first position blocking the respective said vacuum suction tube and a second position opening said respective vacuum suction tube;

means, comprising a single vacuum suction device commonly connected to said second ends of all of said vacuum suction tubes, for, with respect to each said urine suction unit when the respective said valve is in said second position thereof, drawing air into the respective said urine receiver through said air suction hole therein and for drawing air and any urine in said respective urine receiver through the respective said urine outlet and urine transport tube into the respective said urine tank; and each said urine suction unit including control means, connected to the respective said valve and to said single vacuum suction device, for selectively operating said single vacuum suction device and moving said respective valve from said first position thereof to said second position thereof, whereby when each said control means is not operated said respective valve is maintained in said first position thereof and, in the absence of operation of any other of said control means, said single vacuum suction device is stopped.

2. An aid as claimed in claim 1, wherein each said valve comprises a solenoid valve.

* * * * *